(12) United States Patent
Von Arx et al.

(10) Patent No.: US 6,453,196 B1
(45) Date of Patent: Sep. 17, 2002

(54) HIGH FREQUENCY OSCILLATOR FOR IMPLANTABLE MEDICAL DEVICES

(75) Inventors: Jeffrey A. Von Arx, Minneapolis; Ron A. Balczewski, Roseville, both of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 54 days.

(21) Appl. No.: 09/633,549

(22) Filed: Aug. 7, 2000

(51) Int. Cl.[7] .................................................. A61N 1/00
(52) U.S. Cl. ............................................................. 607/9
(58) Field of Search ............................... 341/50, 51, 67, 341/87, 99; 607/9, 5

(56) References Cited

U.S. PATENT DOCUMENTS 4,675,617 A  *  6/1987  Martin
5,570,088 A  *  10/1996  Rhodes

* cited by examiner

Primary Examiner—Scott M. Getzow
(74) Attorney, Agent, or Firm—Nikolai & Mersereau, P.A.; Thomas J. Nikolai

(57) ABSTRACT

A timing circuit especially designed for use in implantable medical devices provides both a low frequency clock and a high frequency clock. The low frequency clock and high frequency clock are compared each time the oscillator producing the high frequency clock is enabled and the result of the comparison is used to retrim the high frequency oscillator to maintain a stable output frequency, even when subjected to drift. Additional circuitry is provided for signaling an oscillator fault in the event that an error signal resulting from the comparison of the low frequency clock with the high frequency clock exceeds a predetermined limit value. Digital trim values are stored for fast and controlled oscillator start-up.

29 Claims, 3 Drawing Sheets

HIGH FREQUENCY OSCILLATOR FOR IMPLANTABLE MEDICAL DEVICES

BACKGROUND OF THE INVENTION

I. Field of the Invention

This invention relates generally to timing circuitry for use in implantable medical devices, such as cardiac rhythm management devices, and more particularly to the design of a high frequency oscillator designed for use in such devices as cardiac pacemakers and automatic implantable cardiac defibrillators (AICDs) which is automatically retrimmed to compensate for frequency drift.

II. Discussion of the Prior Art

Many implantable medical devices (such AICDs) require a high-speed oscillator, operating in the megahertz range, to time a high-speed microprocessor, to run telemetry circuitry within the implanted device and to function as a redundant oscillator for fault detection purposes. These devices will also commonly utilize a low speed oscillator, for example, one operating in the 32 KHz range for timing operations. Given the application in cardiac rhythm management devices that are implanted within the body, the high-speed oscillator used in such devices have several unique requirements. First, the high-speed oscillator must be redundant and must operate independently of the relatively low speed oscillator. A redundant high-speed oscillator allows for effective fault detection in the event that the low speed oscillator should fail in the field. Another requirement for the high-speed oscillator is that it must have a rapid start-up time, providing a clock output within microseconds of its being enabled. Because of size constraints, the high-speed oscillator should have a minimal component count and be conservative of battery power, preferably operating in a microwatt range. Finally, the high-speed oscillator must be stable and as accurate as possible.

In the past, RC oscillators have been used in implementing the high-speed oscillator used in pacemakers and AICDs, principally because the requirements for a fast start-up time and for minimum component count has precluded the use of a crystal-controlled high-speed oscillator. Furthermore, the requirement that the high-speed oscillator operate independent of the low-speed oscillator has prevented the use of a phase-lock loop design. The prior art RC oscillator typically utilize a laser trimmable resistor which, at the time of manufacture, is trimmed so that the high-speed oscillator will produce a desired output frequency, e.g., about 2 MHz. However, this technique does not always produce reliable results in that associated with the external resistor is stray capacitance and trimming of the resistor is found to vary the stray capacitance. This makes it difficult to accurately determine the trimmed resistance value needed. Likewise, where the circuitry is to be encapsulated following the laser-trimming of the resistor, such encapsulation is found to also vary the capacitance across the resistor which, of course, resulted in a change in frequency of the high frequency oscillator from its trimmed value.

It is accordingly a principal object of the present invention to provide an improved high frequency oscillator for implantable medical devices.

Another object of the invention is to provide an improved high frequency oscillator that is automatically retrimmed each time it is enabled to thereby compensate for drift due to temperature changes, noise or component aging.

It is a further object of the present invention to provide a high frequency oscillator for use in implantable medical devices that can be rapidly activated and that automatically undergoes retrimming each time it is enabled to provide improved frequency stability with less components and with lower current drain.

SUMMARY OF THE INVENTION

The foregoing objects and advantages of the invention are realized by providing a timing circuit for an implantable cardiac rhythm management device that comprises a crystal-controlled oscillator for producing an output signal of a predetermined frequency, $f_1$, a second oscillator for producing an output signal of a relatively high frequency, $f_2$, where $f_2 \geq f_1$. The two oscillators each provide an input to a frequency comparator that produces an output that varies proportional to any deviation of the frequency, $f_2$, relative to the stable crystal controlled frequency, $f_1$. The output of the frequency comparator is used in a feedback arrangement to trim the frequency of the non-crystal controlled oscillator to compensate for the deviation, whereby the frequency stability of the non-crystal controlled oscillator is maintained.

The timing circuit further comprises an oscillator fault detector that provides an indication when the deviation of $f_2$ relative to $f_1$ falls outside of predetermined limits.

DESCRIPTION OF THE PREFERRED EMBODIMENT

Figure 1:
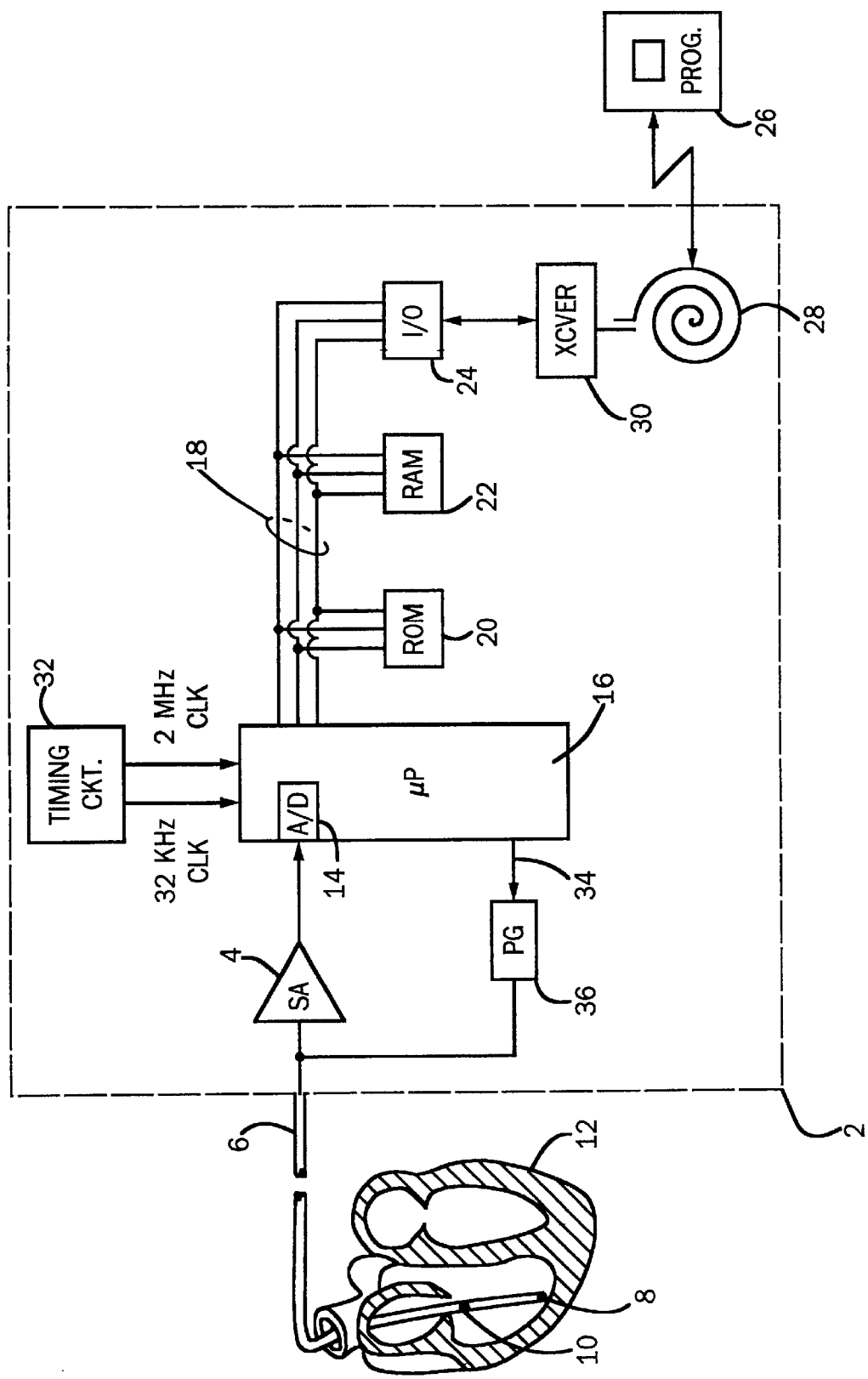
FIG. 1 is a block diagram of a cardiac rhythm management device having the timing circuit of the present invention incorporated therein.

Referring first to FIG. 1, there is schematically illustrated a cardiac rhythm management device for providing stimulating pulses at timed intervals to the heart. Enclosed by the broken line box 2 is a cardiac pacing device comprising a sensing amplifier 4 whose input is connected by a lead 6 to electrodes 8 and 10 shown disposed within the right ventricle of a heart 12. Electrical depolarization signals picked up by the electrodes 8 and 10 are fed through the sense amplifier 4 to an integrated circuit A/D converter 14 shown as being a part of a microprocessor chip 16. The microprocessor chip is operatively connected by a bus 18 to a ROM memory 20, a RAM memory 22 and an input/output (I/O) circuit 24. The I/O circuit 24 acts as an interface allowing bi-directional communication between the implanted CRM module 2 and an external programmer 26. As is known in the art, the programmer 26 will have a telemetry wand that is adapted to be placed over an antenna 28 contained within the implanted device 2 allowing the two-way communication by way of a transceiver circuit 30.

The operation of the microprocessor 16 is controlled by a timing circuit 32 comprising the present invention.

As is known in the art, the ROM memory 20 will typically store a program of instructions executable by the microprocessor 16 while the RAM memory 22 is used to store programmable operands used by the software. The RAM may also be used to store intermediate results of various computations. The output of the microprocessor on line 34 is applied to a pulse generator 36 which then delivers cardiac stimulating pulses over the lead 6 to the heart at times determined by the microprocessor 16.

Figure 2:
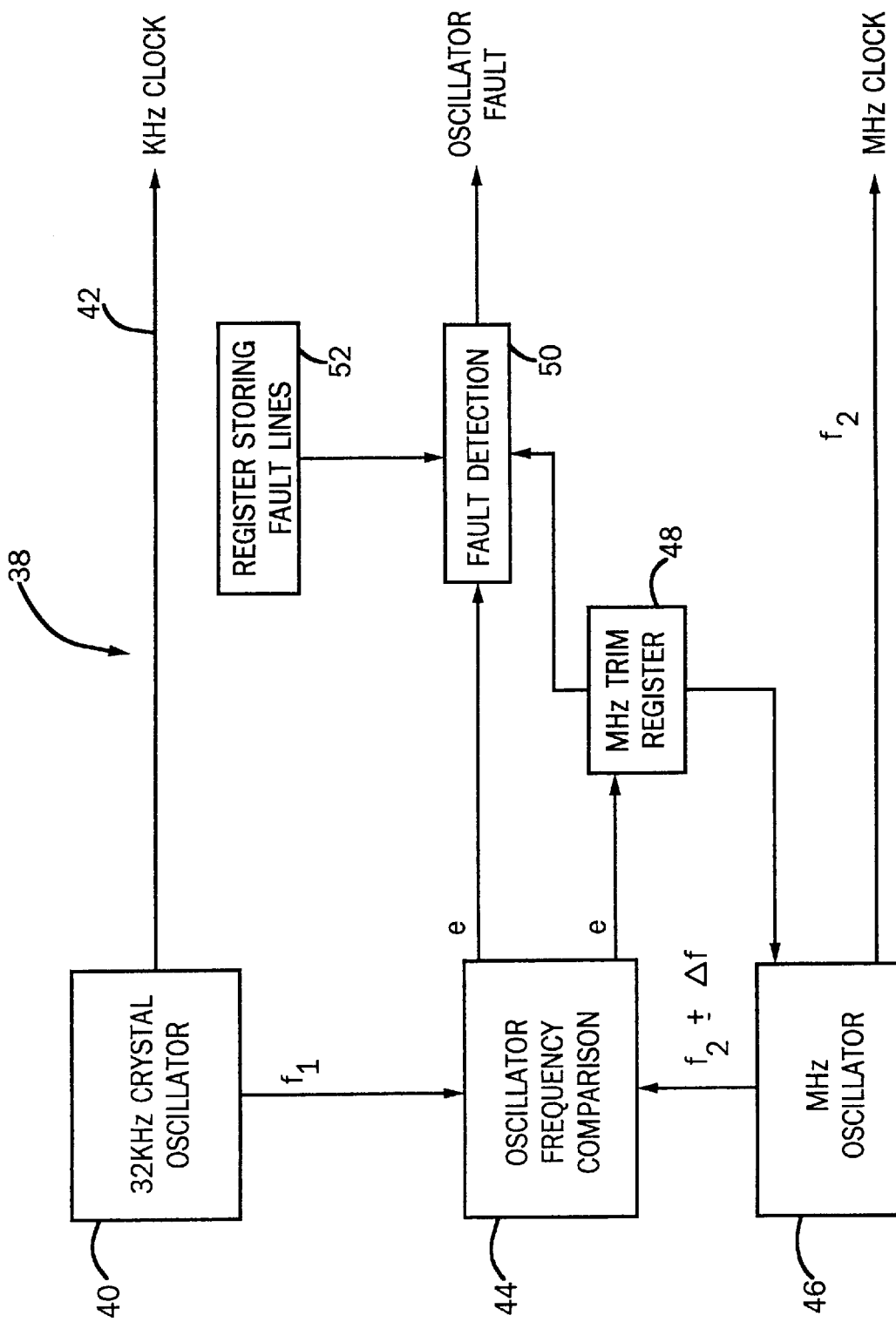
FIG. 2 is a block diagram illustrating a preferred embodiment of the timing circuit of the present invention.

In that the present invention resides primarily in the timing circuit 32, consideration will next be given to the details of construction and operation of that timing circuit. Referring to FIG. 2, there is indicated generally by numeral 38 a timing circuit especially suited for use in an implantable medical device, such as implantable cardiac rhythm management devices, including AICDs and bradycardia pacemakers. As such implantable devices become more computationally intensive, a stable, high-speed oscillator is frequently required for performing clocking functions for the device's high-speed microprocessor and to implement its telemetry circuitry.

As a power conserving measure, the high-speed oscillator generally remains dormant until enabled by the device's microprocessor when certain operations called for by the device's stored program are called for. Upon being enabled, the high-speed oscillator must have a short start-up time so as to output a high frequency clock signal within a few microseconds of being enabled.

The timing circuit 38 may comprise a relatively low speed oscillator 40 that is crystal controlled so as to operate at a fixed frequency, such as, for example, 32 KHz. It runs continuously to produce a 32 KHz clock signal on line 42. The output from the crystal controlled oscillator 40 is also applied to a frequency comparator 44. The comparator 44 receives a second input from an oscillator 46. The frequency of oscillator 46 may be the same as that of oscillator 40, but for most cardiac rhythm management devices will comprise a RC oscillator whose components are adjusted so as to operate in the megahertz range, for example and without limitation, about 2 MHz. RC oscillators possess the requisite fast start-up time.

The oscillator frequency comparator 44 may comprise a digital counter which is enabled periodically to sample (count) pulses arriving from the high speed oscillator 46 during a count interval timed by the low speed oscillator 40. For example, if the counter is turned on for 1 ms based on the low frequency oscillator, the count entered into the counter would be 2,000, assuming that the high frequency oscillator is operating at its 2 MHz rate.

The comparator 44 provides an error input, e, to a trim register 48 that is connected in controlling relation to the high frequency oscillator 46. Should the output frequency of the signal from the high frequency oscillator 18 drift from its nominal 2 MHz rate, there will be an attendant change in the ratio developed by the frequency comparator 44. For example, if it is assumed that due to a temperature change or the like, the frequency of the oscillator 46 varies from its nominal two MHz rate by five percent, the count would change to 1900 for a five percent decrease and to 2100 for a five percent increase. The change in the count from its nominal value (100 in the example) increments or decrements the contents of the trim register 48 which, in turn, adjusts the frequency of the oscillator 46 to compensate for the drift. In this fashion, the oscillator 46 is appropriately trimmed each time that it is enabled and awakened from its dormant state.

A further feature of the timing circuit of the present invention is its ability to signal an oscillator fault whenever the error signal, e, emanating from the frequency comparator 44, exceeds a predetermined limit value. With continued reference to FIG. 2, a fault detection circuit 50 is coupled to receive the output from the frequency comparator 44 and the trim register 48 and tests whether the error signal exceeds predetermined fault limits stored in a programmable register 52. In the event of a catastrophic failure effecting the low frequency oscillator 40, the comparator 44 will output an error signal exceeding the fault limits established by the contents of register 52 and will signal an oscillator fault. Where, however, the failure is not of catastrophic type but instead involves a slower drift, eventually the contents of the trim register 48 will change to the point where the fault limits are exceeded and, again, the fault detection circuit 50 will signal an oscillator fault.

Figure 3:
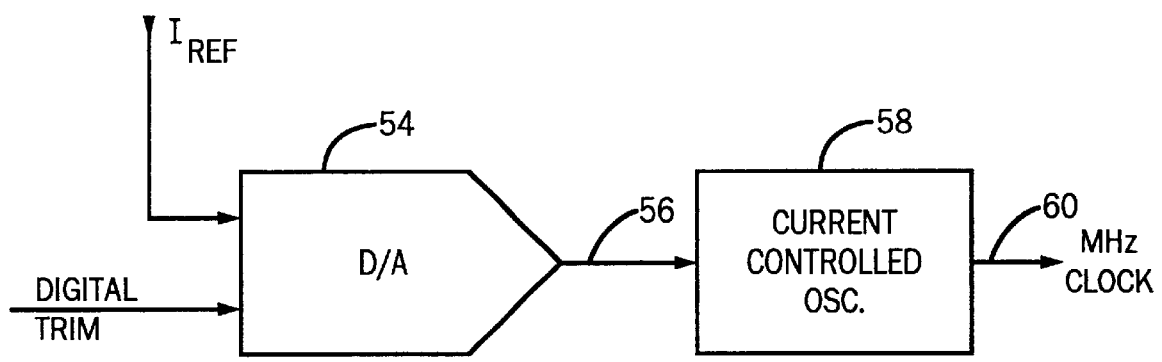
FIG. 3 is a more detailed depiction of the high frequency oscillator of FIG. 1.

Referring next to FIG. 3, there is illustrated the makeup of the megahertz oscillator 46 of FIG. 2. It includes an integrated circuit multiplying digital-to-analog converter 54 which receives as a first input a reference current $I_{ref}$ which may comprise an IPTAT (current proportional to absolute temperature) current source that is available in the battery-powered implantable medical device for biasing various amplifiers and the circuitry. The second input to the digital-to-analog converter 54 comprises the contents of the trim register 48.

As is known in the art, digital codes are typically converted to analog voltages or currents by assigning a weight to each bit in the digital code and then summing the weights of the entire code. Generally speaking, a typical D/A converter consists of a network of precision resistors, input switches and level shifters to activate the switches to convert a digital code to an analog current or voltage. Being a multiplying D/A converter, the device 54 produces an output signal that is proportional to the product of the reference, $I_{ref}$, times the digital code from the trim register 48.

The output current on line 56 of the D/A converter is applied to a current controlled oscillator 58 and, as such, the megahertz clock output signal on line 60 is adjusted in accordance with the contents of the trim register 48. In that the contents of the trim register 48 are periodically updated by the oscillator frequency comparator 44, the high-speed current-controlled oscillator 58 periodically automatically retrims itself so as to compensate for drift. In that no off-chip resistor is required for trimming purposes, it occupies less physical space allowing for greater miniaturization of the implant device. Furthermore, the design has the fault detection capability of two independent oscillators in that hard limits are set on the adjustable range of the high-speed oscillator. Should the trim value, e, fall outside of the hard limits established by the contents of register 52, the timing circuit of the present invention will generate an oscillator fault. When an oscillator fault occurs, the system goes into a fail-safe state until the fault condition is removed.

The high-speed current controlled oscillator 58 described starts up quickly when enabled in that it stores in a digital memory the most recent trim setting and returns to that setting when enabled. The reference current $I_{ref}$ applied to the D/A converter 54 is tapped off from an IPTAT current source already available in the implantable medical device, thus obviating the need for a separate resistor to generate a reference current. Moreover, because the high-speed oscillator described herein retrims itself periodically, it will automatically compensate for temperature, allowing the device's temperature varying current source to be used for the oscillator as well as for the device's amplifiers and other circuitry.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself

What is claimed is:

1. A timing circuit for an implantable medical device comprising, in combination:
   (a) a crystal controlled oscillator for producing an output signal of a frequency $f_1$;
   (b) a non-crystal controlled oscillator for producing an output signal of a frequency $f_2$, where $f_2 \geqq f_1$;
   (c) a frequency comparator connected to receive the output signals $f_1$ and $f_2$ and producing an output that varies proportional to any deviation of $f_2$ relative to $f_1$; and
   (d) a control circuit responsive to the output of the frequency comparator and connected to the non-crystal controlled oscillator that trims the frequency of the non-crystal controlled oscillator to compensate for said deviation.

2. The timing circuit of claim 1 and further including:
   (a) an oscillator fault detector providing an indication when the deviation of $f_2$ relative to $f_1$ falls outside of predetermined limits.

3. The timing circuit of claim 1 wherein the crystal controlled oscillator is continuously running and the non-crystal controlled oscillator runs intermittently.

4. The timing circuit of claim 1 wherein the control circuit comprises,
   (a) a register for storing a digital trim value; and
   (b) a digital-to-analog converter coupled to receive the digital trim value, the output of the digital-to-analog converter coupled to provide a control signal to the non-crystal controlled oscillator to vary the frequency thereof.

5. The timing circuit of claim 4 wherein the digital-to-analog converter is a multiplying digital-to-analog converter coupled to receive the digital trim value and a reference input.

6. The timing circuit of any one of claims 1–5 wherein where $f_2 >> f_1$.

7. The timing circuit of claim 6 wherein where $f_1$ is about 32 KHz and where $f_2$ is about 2 MHz.

8. A method of continuously trimming the operating frequency of a high-speed oscillator comprising the steps of
   (a) providing a continuously running, stable, relatively low speed crystal-controlled oscillator;
   (b) providing an intermittently running relatively high-speed non-crystal controlled oscillator that produces an output signal that is subject to frequency drift;
   (c) comparing the frequency of the output signal of the high-speed oscillator to the frequency of the output from the low-speed oscillator and producing a trim-adjusting value proportional to any deviation of the frequency of the output signal of the high-speed oscillator from the frequency of the low-speed oscillator; and
   (d) applying a current proportional to an adjusted trim value to the high-speed oscillator to adjust its output signal to compensate for any frequency deviation of the high speed oscillator.

9. The method of claim 8 and further including:
   (a) comparing the trim adjusting value to a predetermined limit; and
   (b) signaling an oscillator fault upon the trim adjusting value equaling or exceeding the limit.

10. A timing circuit for an implantable cardiac rhythm management device comprising:
    (a) first oscillator means for producing an AC signal of frequency $f_1$;
    (b) second oscillator means for producing an AC signal of a frequency where $f_2 \geqq f_1$;
    (c) means for detecting any deviation of the frequency of the second oscillator means from the frequency $f_2$;
    (d) means responsive to the detecting means for trimming the second oscillator, such that the frequency deviation of the second oscillator is minimized; and
    (e) means for signaling fault condition when the deviation in frequency of the second oscillator means equals or exceeds a predetermined limit.

11. The timing circuit of claim 10 and further including:
    (a) storage means coupled to the deviation detection means for storing a latest trim value for the second oscillator, said latest trim value being used to control the frequency of the second oscillator upon start-up of the second oscillator following a shut-down thereof.

12. A digitally trimmable oscillator system comprising:
    (a) a stable crystal controlled oscillator for producing an output signal of a predetermined frequency;
    (b) a second non-crystal controlled oscillator whose output signal is subject to frequency drift; and
    (c) a digital feedback control circuit for adjusting the frequency of the output signal of the second oscillator based on a detected deviation of the frequency of the output signal of the second oscillator from said predetermined frequency.

13. The digitally trimmable oscillator system of claim 12 wherein the digital feedback control circuit comprises:
    (a) a counter coupled to receive and count input pulses from the second oscillator during a time interval determined by the stable oscillator;
    (b) a trim register for storing count values from said counter; and
    (c) a digital to analog converter coupling the trim register to the second oscillator for supplying a current to the second oscillator proportional to the count value in the trim register.

14. The digitally trimmable oscillator system of claim 13 and further including:
    (a) fault detection means for signaling an oscillatory system fault condition when the count value deviates from a predetermined nominal value by a predetermined error limit.

15. The digitally trimmable oscillator system of claim 13 wherein the second oscillator is periodically enabled and disabled and each time enabled, starts at a frequency determined by the then content of the trim register.

16. A cardiac rhythm management device comprising:
    (a) a sense amplifier connected to receive cardiac depolarization signals from a patient's heart,
    (b) a pulse generator for applying cardiac stimulating pulses to the heart at timed intervals;
    (c) a microprocessor coupled to the sense amplifier for receiving cardiac depolarization information and responsive thereto for supplying control signals to the pulse generator in accordance with a software program; and
    (d) a timing circuit for supplying clocking pulses to the microprocessor of a first frequency, $f_1$ and a second higher frequency, $f_2$, the timing circuit including a feedback circuit that compares fi to $f_2$ and adjusts $f_2$ to compensate for any drift in frequency of $f_2$ relative to $f_1$.

17. The cardiac rhythm management device of claim 16 wherein the timing circuit further includes a fault detection circuit coupled to the feedback circuit for signaling a fault condition when the deviation of $f_2$ relative to $f_1$ exceeds a predetermined limit value.

18. The cardiac rhythm management device of claim 16 wherein the timing circuit comprises:
   (a) a crystal controlled oscillator for producing the clocking devices of frequency, $f_1$;
   (b) a current controlled oscillator for producing the clocking pulses of frequency, $f_2$;
   (c) said feedback circuit including a counter coupled to receive the clocking pulses of frequencies, $f_1$ and $f_2$, and tallying the number of clocking pulses of frequency, $f_2$, occurring between clocking pulses of frequency, $f_1$, and a trim register coupled to the counter for storing the tally; and
   (d) a digital-to-analog converter coupled to the trim register for producing a control current for the current controlled oscillator proportional to the tally stored in the trim register.

19. The cardiac rhythm management device of claim 18 and further including a fault detection circuit coupled to the counter and to the trim register for signaling a fault condition when the deviation of $f_2$ relative to $f_1$ exceeds a predetermined limit value.

20. A timing circuit for an implantable medical device comprising, in combination:
   (a) a crystal controlled oscillator for producing an output signal of a frequency $f_1$;
   (b) a further oscillator for producing an output signal of a frequency $f_2$, where $f_2 \geq f_1$;
   (c) a frequency comparator connected to receive the output signals $f_1$ and $f_2$ and producing an output that varies proportional to any deviation of $f_2$ relative to $f_1$;
   (d) a control circuit responsive to the output of the frequency comparator and connected to the further oscillator that trims the frequency of the further oscillator to compensate for said deviation; and
   (e) an oscillator fault detector providing an indication when the deviation of $f_2 \geq f_1$ falls outside of predetermined limits.

21. The timing circuit of claim 20 wherein the crystal controlled oscillator is continuously running and the further oscillator runs intermittently.

22. The timing circuit of claim 20 wherein the control circuit comprises;
   (a) a register for storing a digital trim value; and
   (b) a digital-to-analog converter coupled to receive the digital trim value, the output of the digital-to-analog converter coupled to provide a control signal to the further oscillator to vary the frequency thereof.

23. The timing circuit of claim 22 wherein the digital-to-analog converter is a multiplying digital-to-analog converter coupled to receive the digital trim value and a reference input.

24. The timing circuit of any one of claims 20–23 wherein $f_2$ is $>>f_1$.

25. The timing circuit of claim 24 wherein where $f_1$ is about 32 KHz and where $f_2$ is about 2 MHz.

26. A method of continuously trimming the operating frequency of a high-speed oscillator comprising the steps of:
   (a) providing a continuously running, stable, relatively low speed oscillator,
   (b) providing an intermittently running relatively high-speed oscillator that produces an output signal that is subject to frequency drift;
   (c) comparing the frequency of the output signal of the high-speed oscillator to the frequency of the output from the low-speed oscillator and producing a trim-adjusting value proportional to any deviation of the frequency of the output signal of the high-speed oscillator from the frequency of the low-speed oscillator;
   (d) applying a current proportional to an adjusted trim value to the high-speed oscillator to adjust its output signal to compensate for any frequency deviation of the high speed oscillator;
   (e) comparing the trim adjusting value to a predetermined limit; and
   (f) signaling an oscillator fault upon the trim adjusting value equaling or exceeding the limit.

27. A digitally trimmable oscillator system comprising:
   (a) a stable oscillator for producing an output signal of a predetermined frequency;
   (b) a second oscillator whose output signal is subject to frequency drift;
   (c) a digital feedback control circuit for adjusting the frequency of the output signal of the second oscillator based on a detected deviation of the frequency of the output signal of the second oscillator from said predetermined frequency, said digital feedback control circuit including
      (i) a counter coupled to receive and count input pulses from the second oscillator during a time interval determined by the stable oscillator;
      (ii) a trim register for storing count values from said counter, and
      (iii) a digit-to-analog converter coupling the trim register to the second oscillator for supplying a current to the second oscillator proportional to the count value in the trim register.

28. The digitally trimmable oscillator system of claim 27 and further including:
   (a) fault detection means for signaling an oscillatory system fault condition when the count value deviates from a predetermined nominal value by a predetermined error limit.

29. The digitally trimmable oscillator system of claim 27 wherein the second oscillator is periodically enabled and disabled and each time enabled, starts at a frequency determined by the then content of the trim register.

* * * * *